United States Patent [19]

Shida et al.

[11] Patent Number: 4,968,345
[45] Date of Patent: Nov. 6, 1990

[54] PHENYLHYDRAZONE DERIVATIVE OF OXAMIDE AND HERBICIDAL COMPOSITION CONTAINING THE SAME

[75] Inventors: Takafumi Shida; Hideo Arabori; Takeo Watanabe; Yoichi Kanda; Shiro Yamazaki; Hiroyasu Shinkawa, all of Iwaki, Japan

[73] Assignee: Kureha Kagaku Kogyo Kabushiki Kaishi, Tokyo, Japan

[21] Appl. No.: 162,934

[22] Filed: Mar. 2, 1988

[30] Foreign Application Priority Data

Mar. 20, 1987 [JP] Japan .................... 62-66725

[51] Int. Cl.$^5$ .................. A01N 47/40; C07C 257/22
[52] U.S. Cl. .................... 71/118; 464/149; 464/150
[58] Field of Search .................. 564/149, 150; 71/118

[56] References Cited

U.S. PATENT DOCUMENTS

3,641,098  2/1972  Buchel et al. .................. 564/149 X

FOREIGN PATENT DOCUMENTS

0220956  10/1986  European Pat. Off. .

OTHER PUBLICATIONS

Tetrahedron, vol. 31, No. 1, 1975, pp. 25–29.
"Triazoles, Part VI, 1,5-Diaryl-1,2,4-triazole-3-aldehydes", by Browne et al., *Journal of the Chemical Society*, 1962, p. 575–583.

*Primary Examiner*—Carolyn S. Elmore
*Attorney, Agent, or Firm*—Nixon & Vanderhye

[57] ABSTRACT

Disclosed herein is a phenylhydrazone derivative of oxamide represented by the formula (I):

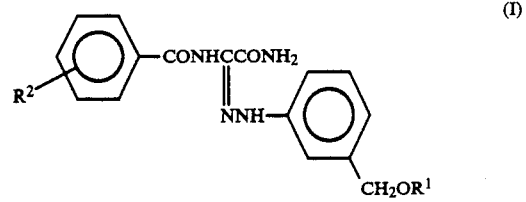

wherein $R^1$ is straight-chain alkyl group having 2 to 10 carbon atoms, branched alkyl group or cyclic alkyl group having 3 to 10 carbon atoms, alkyl group having 1 to 3 carbon atoms which is substituted with an alicyclic structure having 3 to 7 carbon atoms, phenyl group, halogen-substituted phenyl group, aralkyl group having 7 to 9 carbon atoms, alkenyl group having 3 to 6 carbon atoms, alkyl group having 2 to 4 carbon atoms which is substituted with alkoxy group having 1 to 4 carbon atoms, or alkyl group having 2 to 10 carbon atoms which is substituted with 1 to 19 fluorine atoms; and $R^2$ is hydrogen, fluorine, chlorine, methyl group or methoxy group, and a herbicidal composition containing the derivative as active ingredient. The phenylhydrazone derivative of oxamide represented by the formula (I) of the present invention shows a high herbicidal activity and also have an excellent selectivity allowing killing of weeds alone without doing any practical harm to the crops such as rice, wheat and corn.

9 Claims, No Drawings

PHENYLHYDRAZONE DERIVATIVE OF OXAMIDE AND HERBICIDAL COMPOSITION CONTAINING THE SAME

BACKGROUND OF THE INVENTION

The present invention relates to a phenylhydrazone derivative of oxamide useful as active ingredient of herbicidal composition and to the herbicidal compositions containing said derivatives as active ingredient.

Hitherto, 1-(2-tolyl)hydrazone of N-benzoyloxamide and 1-(3-tolyl)hydrazone of N-benzoyloxamide have been reported as phenylhydrazone derivatives of oxamide (Journal of the Chemical Society, 575, 1962). However, no disclosure has ever been made about the phenylhydrazone derivatives of oxamide represented by the following formula (I):

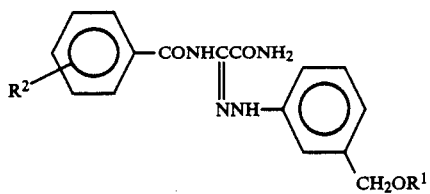

(wherein $R^1$ is straight-chain alkyl group having 2 to 10 carbon atoms, branched alkyl group or cyclic alkyl group having 3 to 10 carbon atoms, alkyl group having 1 to 3 carbon atoms which is substituted with an alicyclic structure having 3 to 7 carbon atoms, phenyl group, halogen-substituted phenyl group, aralkyl group having 7 to 9 carbon atoms, alkenyl group having 3 to 6 carbon atoms alkyl group having 2 to 4 carbon atoms which is subsutituted with alkoxy group having 1 to 4 carbon atoms, or alkyl group having 2 to 10 carbon atoms which is substituted with 1 to 19 fluorine atoms; and $R^2$ is hydrogen, fluorine, chlorine, methyl group or methoxy group, and the fact that such derivatives have an excellent selective herbicidal activity.

Rice, wheat and corn are the important crops, and use of a herbicide is essential for increasing the yield of such crops by protecting them against harm by weeds. Thus, the development of the herbicides, especially the ones having a selective herbicidal activity enabling killing of weeds alone without doing any practical harm to the crops even if applied to the crops and weeds at the same time, has been strongly desired.

The present inventors have made extensive studies on the compounds showing an excellent herbicidal effect but not doing any practical harm to the useful crops such as rice, wheat and corn, and found that the phenylhydrazone derivatives of oxamide represented by the following formula (I) have the excellent selective herbicidal activities:

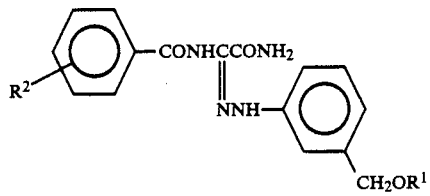

wherein $R^1$ is straight-chain alkyl group having 2 to 10 carbon atoms, branched alkyl group or cyclic alkyl group having 3 to 10 carbon atoms, alkyl group having 1 to 3 carbon atoms which is substituted with an alicyclic structure having 3 to 7 carbon atoms, phenyl group, halogen-substituted phenyl group aralkyl group having 7 to 9 carbon atoms, alkenyl group having 3 to 6 carbon atoms, alkyl group having 2 to 4 carbon atoms which is substituted with alkoxy group having 1 to 4 carbon atoms, or alkyl group having 2 to 10 carbon atoms which is substituted with 1 to 19 fluorine atoms; and $R^2$ is hydrogen, fluorine, chlorine, methyl group or methoxy group.

The present invention was attained on the basis of this finding.

Thus, the present invention has for its object to provide a phenylhydrazone derivative of oxamide having a selective herbicidal activity, that is, showing excellent herbicidal activities against the gramineous weeds and, in particular, broadleaf weeds, while doing no harm to the crops such as rice, wheat and corn, and a herbicidal composition containing such derivatives as active ingredient.

SUMMARY OF THE INVENTION

In a first aspect of the present invention, there is provided a phenylhydrazone derivative of oxamide represented by the formula (I):

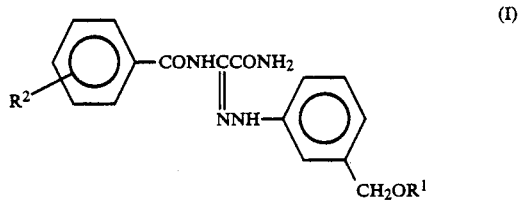

wherein $R^1$ is straight-chain alkyl group having 2 to 10 carbon atoms, branched alkyl group or cyclic alkyl group having 3 to 10 carbon atoms, alkyl group having 1 to 3 carbon atoms which is substituted with an alicyclic structure having 3 to 7 carbon atoms, phenyl group, halogen-substituted phenyl group, aralkyl group having 7 to 9 carbon atoms, alkenyl group having 3 to 6 carbon atoms, alkyl group having 2 to 4 carbon atoms which is substituted with alkoxy group having 1 to 4 carbon atoms, or alkyl group having 2 to 10 carbon atoms which is substituted with 1 to 19 fluorine atoms; and $R^2$ is hydrogen, fluorine, chlorine, methyl group or methoxy group.

In a second aspect of the present invention, there is provided a herbicidal composition comprising as active ingredient a herbicidally effective amount of a phenylhydrazone derivative of oxamide represented by the formula (I):

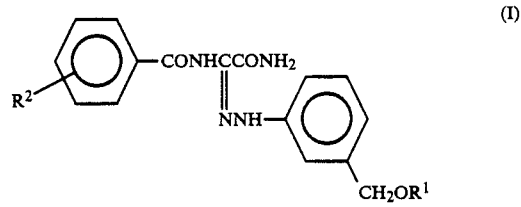

wherein $R^1$ and $R^2$ are as defined above, and herbicidally acceptable carrier or adjuvant.

In a third aspect of the present invention, there is provided a process for producing a phenylhydrazone derivative of oxamide represented by the formula (I):

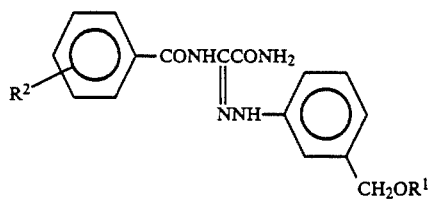

wherein $R^1$ and $R^2$ are as defined above, which comprises reacting phenylhydrazone derivative of 2-oxazoline-4,5-dione represented by the formula (II):

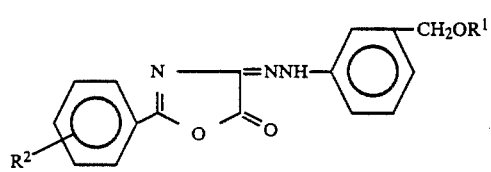

wherein $R^1$ and $R^2$ are as defined above, with ammonia in an organic solvent at a temperature of $-10°$ to $100°$ C.

DETAILED DESCRIPTION OF THE INVENTION

The present invention relates to a phenylhydrazone derivative of oxamide represented by the formula (I):

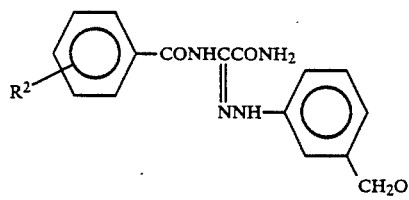

and a herbicidal composition containing such derivative as active ingredient.

In the above-shown formula (I), $R^1$ represents straight-chain alkyl group having 2 to 10, preferably 3 to 6 carbon atoms, branched alkyl or cyclic alkyl group having 3 to 10, preferably 3 to 7 carbon atoms, alkyl group having 1 to 3, preferably 1 to 2 carbon atoms, which is substituted with an alicyclic structure having 3 to 7, preferably 3 to 6 carbon atoms, phenyl group, phenyl group substituted with preferably 1 to 3 halogens, aralkyl group having 7 to 9 carbon atoms, alkenyl group having 3 to 6 carbon atoms, alkyl group having 2 to 4, preferably 2 carbon atoms, which is substituted with alkoxyl group having 1 to 4, preferably 4 carbon atoms, or alkyl group having 2 to 10, preferably 2 to 6 carbon atoms, which is substituted with 1 to 19, preferably 3 to 12 fluorine atoms; and $R^2$ represents hydrogen, fluorine, chlorine, methyl or methoxyl group.

The compounds represented by the formula (I) of the present invention, their physicochemical properties and the results of their elemental analyses are shown in Tables 1 and 2.

TABLE 1

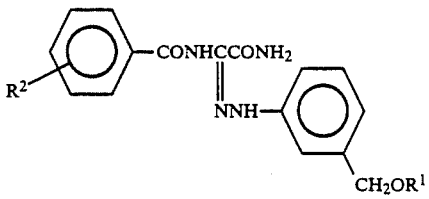

| No. | $R^1$ | $R^2$ |
|---|---|---|
| 1 | $-(CH_2)_3CH_3$ | H |
| 2 | $-(CH_2)_4CH_3$ | H |
| 3 | $CH_3$<br>$-CH_2CHCH_2CH_3$ | H |
| 4 | $-CH_2C(CH_3)_3$ | H |
| 5 | $-CH_2-\langle H \rangle$ (cyclohexyl) | H |
| 6 | $-\langle\bigcirc\rangle$ (phenyl) | H |
| 7 | (phenyl) | H |
| 8 | $-CH_2-\langle\bigcirc\rangle$ (benzyl) | H |
| 9 | $-CH_2CH=CH_2$ | H |
| 10 | $-CH_2CF_3$ | H |
| 11 | $-CH_2CF_2CHF_2$ | H |
| 12 | $-CH_2(CF_2)_3CHF_2$ | H |
| 13 | $-CH_2(CF_2)_5CHF_2$ | H |
| 14 | $-(CH_2)_2O(CH_2)_3CH_3$ | H |
| 15 | $-(CH_2)_3CH_3$ | 2-F |
| 16 | $-(CH_2)_4CH_3$ | 2-F |
| 17 | $-(CH_2)_2CH(CH_3)_2$ | 2-F |
| 18 | $-(CH_2)_2CH(CH_3)_2$ | 3-F |
| 19 | $-(CH_2)_2CH(CH_3)_2$ | 4-F |
| 20 | $CH_3$<br>$-CH_2CHCH_2CH_3$ | 2-F |
| 21 | $-CH_2C(CH_3)_3$ | 2-F |
| 22 | $-(CH_2)_5CH_3$ | 2-F |
| 23 | $-CH_2-\langle H\rangle$ (cyclohexyl) | 2-F |
| 24 | (phenyl) | 2-F |
| 25 | $-\langle\bigcirc\rangle-F$ | 2-F |

TABLE 1-continued

Structure (I): R²-C₆H₄-CONHCCONH₂ with =NNH- linked to phenyl bearing CH₂OR¹

| No. | R¹ | R² |
|---|---|---|
| 26 | 4-Cl-phenyl | 2-F |
| 27 | —CH₂-phenyl | 2-F |
| 28 | —CH₂CH=CH₂ | 2-F |
| 29 | —CH₂CF₃ | 2-F |
| 30 | —CH₂CF₂CHF₂ | 2-F |
| 31 | —CH₂CF₂CF₃ | 2-F |
| 32 | —CH₂CF₂CF₃ | 3-F |
| 33 | —CH₂CF₂CF₃ | 4-F |
| 34 | —CH₂CF₂CHFCF₃ | 2-F |
| 35 | —CH₂(CF₂)₂CF₃ | 2-F |
| 36 | —CH₂(CF₂)₂CF₃ | 3-F |
| 37 | —CH₂(CF₂)₂CF₃ | 4-F |
| 38 | —CH₂(CF₂)₃CHF₂ | 2-F |
| 39 | —CH₂(CF₂)₅CHF₂ | 2-F |
| 40 | —(CH₂)₂CH(CH₃)₂ | 4-Cl |
| 41 | —CH₂CF₂CF₃ | 4-Cl |
| 42 | —CH₂(CF₂)₂CF₃ | 4-Cl |
| 43 | —(CH₂)₂CH(CH₃)₂ | 4-CH₃ |
| 44 | —CH₂CF₂CF₃ | 4-CH₃ |
| 45 | —CH₂(CF₂)₂CF₃ | 4-CH₃ |
| 46 | —(CH₂)₂CH(CH₃)₂ | 4-OCH₃ |
| 47 | —CH₂(CF₂)₂CF₃ | 4-OCH₃ |

TABLE 2

| Compound No. | Melting point (°C.) | IR (KBr, cm⁻¹) and NMR [d₆-DMSO, δ, ppm, 60 MHz] (*CDCl₃ was used) | Elemental analysis Found / Calcd. C (%) | H (%) | N (%) |
|---|---|---|---|---|---|
| 1 | 145–6 | IR: 3460 3310 3250 1680 1630 NMR: 0.83 (3H, t, 6 Hz) 0.91–1.66 (4H, m) 3.36 (2H, t, 6 Hz) 4.35 (2H, s) 6.63–6.96 (1H, bs) 6.98–7.66 (8H, m) 7.83–8.1 (2H, m) 9.56 (1H, s) 9.73 (1H, s) | Found 65.00% / Calcd. 65.20% | 6.63% / 6.57% | 15.40% / 15.21% |
| 2 | 128–31 | IR: 3460 3310 3250 1680 1635 NMR: 0.83 (3H, t, 7 Hz) 1.0–1.73 (6H, m) 3.36 (2H, t, 7 Hz) 4.36 (2H, s) 6.6–6.88 (1H, bs) 6.88–7.68 (8H, m) 7.83–8.1 (2H, m) 9.56 (1H, s) 9.7 (1H, s) | Found 65.90% / Calcd. 65.95% | 6.74% / 6.85% | 14.83% / 14.65% |
| 3 | 135–7 | IR: 3460 3310 3250 1680 1635 NMR: 0.8 (3H, t, 6 Hz) 0.86 (3H, d, 6 Hz) 1–1.93 (3H, m), 3.23 (2H, d, 6 Hz) 4.36 (2H, s) 6.65–6.95 (1H, bs) 6.97–7.66 (8H, m) 7.83–8.13 (2H, m) 9.6 (1H, s) 9.73 (1H, s) | Found 65.91% / Calcd. 65.95% | 6.65% / 6.85% | 14.49% / 14.65% |
| 4 | 118–20 | IR: 3470 3310 3260 2950 2850 1685 1640 NMR: 0.88 (9H, s) 3.08 (2H, s) 4.41 (2H, s) 6.63–6.95 (1H, bs) 6.95–7.68 (8H, m) 7.85–8.1 (2H, m) 9.6 (1H, bs) 9.75 (1H, bs) | Found 65.93% / Calcd. 65.95% | 7.00% / 6.85% | 14.83% / 14.65% |
| 5 | 157–8 | IR: 3460 3320 3260 2910 2840 1680 1640 NMR: 0.55–1.95 (11H, m) 3.15 (2H, m) 4.33 (2H, s) 6.58–6.9 (1H, bs) 7.0–7.66 (8H, m) 7.8–8.1 (2H, m) 9.55 (1H, s) 9.7 (1H, s) | Found 67.48% / Calcd. 67.63% | 6.90% / 6.91% | 13.54% / 13.71% |
| 6 | 185–7 | IR: 3470 3320 3250 1680 1630 NMR: 5.0 (2H, s) 6.36–6.73 (1H, bs) 6.73–7.63 (13H, m) 7.76–8.06 (2H, m) 9.6 (1H, s) 9.76 (1H, s) | Found 68.23% / Calcd. 68.03% | 5.39% / 5.19% | 14.37% / 14.42% |
| 7 | 181–2 | IR: 3440 3340 3170 1680 1657 NMR: 5.0 (2H, s) 6.6–7.66 (9H, m) 6.73 (2H, d, 9 Hz) 7.26 (2H, d, 9 Hz) 7.76–8.11 (2H, m) 9.56 (1H, s) 9.73 (1H, s) | Found 62.55% / Calcd. 62.49% | 4.72% / 4.53% | 13.35% / 13.25% |
| 8 | 131–3 | IR: 3460 3310 3250 1680 1635 NMR: 4.45 (2H, s) 4.5 (2H, s) 6.71–6.96 (1H, bs) 6.97–7.66 (13H, m) 7.86–8.11 (2H, m) 9.6 (1H, s) 9.76 (1H, s) | Found 68.84% / Calcd. 68.64% | 5.31% / 5.51% | 14.09% / 13.92% |
| 9 | 162–3 | IR: 3470 3310 3250 1680 1635 NMR: 3.93 (2H, d, 5 Hz) 4.38 (2H, s) 4.96–5.41 (2H, m) 5.51–6.2 (1H, m) 6.6–6.96 (1H, bs) 7.0–7.7 (8H, m) 7.86–8.1 (2H, m) 9.5 (1H, s) 9.7 (1H, s) | Found 64.85% / Calcd. 64.76% | 5.84% / 5.72% | 16.09% / 15.90% |
| 10 | 171–2 | IR: 3460 3260 1680 1630 NMR: 4.0 (2H, q, 9 Hz) 4.56 (2H, s) | Found 55.02% / Calcd. 54.82% | 4.24% / 4.35% | 14.08% / 14.21% |

TABLE 2-continued

| Compound No. | Melting point (°C.) | IR (KBr,cm$^{-1}$) and NMR [d$_6$-DMSO, δ, ppm, 60 MHz] (*CDCl$_3$ was used) | Elemental analysis | | | |
|---|---|---|---|---|---|---|
| | | | Found Calcd. | C (%) | H (%) | N (%) |
| | | 6.63–6.96 (1H, bs) 6.96–7.66 (8H, m) 7.83–8.1 (2H, m) 9.58 (1H, bs) 9.75 (1H, bs) | | | | |
| 11 | 126–8 | IR: 3450 3340 3260 1675 1635 NMR: 3.92 (2H, tt, 14 Hz, 2 Hz) 4.58 (2H, s) 6.50 (1H, tt, 53 Hz, 6 Hz) 6.72–8.18 (11H, m) 9.68 (1H, s) 9.82 (1H, s) | Found Calcd. | 53.71% 53.52% | 4.06% 4.26% | 13.04% 13.14% |
| 12 | 96–8 | IR: 3460 3390 3250 1680 1635 NMR: 4.08 (2H, tt, 15 Hz, 2 Hz) 5.08 (2H, s) 6.08 (1H, tt, 54 Hz, 6 Hz) 6.50–8.25 (11H, m) 9.65 (1H, s) 9.80 (1H, s) | Found Calcd. | 48.12% 47.92% | 3.46% 3.45% | 10.57% 10.64% |
| 13 | 104–6 | IR: 3460 3390 3270 1680 1635 NMR: 4.15 (2H, tt, 15 Hz, 2 Hz) 4.60 (2H, s) 6.28 (1H, tt, 51 Hz, 5 Hz) 6.6–8.33 (11H, m) 9.70 (1H, s) 9.85 (1H, s) | Found Calcd. | 44.29% 44.10% | 2.77% 2.90% | 9.14% 8.94% |
| 14 | 110 | IR: 3460 3310 3250 1680 1630 NMR: 0.85 (3H, t, 7 Hz) 1–1.63 (4H, m) 3.3–3.6 (6H, m) 4.41 (2H, s) 6.53–6.93 (1H, bs) 6.93–7.65 (8H, m) 7.78–8.1 (2H, m) 9.6 (1H, bs) 9.73 (1H, bs) | Found Calcd. | 64.01% 64.06% | 6.71% 6.84% | 13.45% 13.58% |
| 15 | 133–5 | IR: 3460 3330 3240 1680 1630 NMR: 0.9 (3H, t, 6 Hz) 1.13–1.9 (4H, m) 3.45 (2H, t, 6 Hz) 4.45 (2H, s) 5.6 (1H, bs) 6.75–7.7 (8H, m) 7.93–8.3 (1H, m) 9.6–10.3 (2H, m) | Found Calcd. | 62.09% 62.17% | 5.94% 6.00% | 14.59% 14.50% |
| 16 | 125–8 | IR: 3470 3350 3240 1680 1635 NMR: 0.85 (3H, t, 5 Hz) 1.06–1.76 (6H, m) 3.26–3.53 (2H, m) 4.38 (2H, s) 6.6–8.03 (10H, m) 9.46 (1H, bs) 9.7 (1H, bs) | Found Calcd. | 63.19% 62.99% | 6.31% 6.29% | 14.19% 13.99% |
| 17 | 138–40 | IR: 3475 3350 3250 1680 1640 NMR*: 0.88 (6H, d, 6 Hz) 1.33–2 (3H, m) 3.5 (2H, t, 6 Hz) 4.45 (2H, s) 5.56 (1H, bs) 6.8–7.75 (8H, m) 7.96–8.36 (1H, m) 9.8–10.3 (2H, m) | Found Calcd. | 63.18% 62.99% | 6.29% 6.29% | 14.12% 13.99% |
| 18 | 110–5 | IR: 3450 3260 1680 1630 1460 NMR: 0.83 (6H, d, 6 Hz) 1.16–1.8 (3H, m) 3.4 (2H, t, 6 Hz) 4.33 (2H, s) 6.58–7.9 (10H, m) 9.63 (1H, bs) 9.66 (1H, bs) | Found Calcd. | 63.12% 62.99% | 6.31% 6.29% | 14.16% 13.99% |
| 19 | 126–8 | IR: 3450 3250 1680 1630 NMR: 0.85 (6H, d, 6 Hz) 1.1–1.71 (3H, m) 3.38 (2H, t, 6 Hz) 4.33 (2H, s) 6.5–7.53 (8H, m) 7.83–8.16 (2H, m) 9.53 (1H, bs) 9.63 (1H, bs) | Found Calcd. | 63.15% 62.99% | 6.30% 6.29% | 14.14% 13.99% |
| 20 | 131–3 | IR: 3470 3345 3250 1685 1640 NMR: 0.8 (3H, t, 6 Hz) 0.86 (3H, d, 6 Hz) 1–1.93 (3H, m) 3.20 (2H, d, 6 Hz) 4.33 (2H, s) 6.63–7.83 (10H, m) 9.63 (1H, s) 9.60 (1H, s) | Found Calcd. | 63.18% 62.99% | 6.31% 6.29% | 13.81% 13.99% |
| 21 | 155–6 | IR: 3460 3340 3240 1680 1635 NMR: 0.9 (9H, s) 3.08 (2H, s) 4.43 (2H, s) 6.6–7 (1H, m) 7–7.93 (9H, m) 9.46 (1H, bs) 9.66 (1H, s) | Found Calcd. | 63.10% 62.99% | 6.30% 6.29% | 13.88% 13.99% |
| 22 | 127–9 | IR: 3480 3350 3250 2920 2850 1680 1630 NMR: 0.87 (3H, t, 6 Hz) 1.07–1.77 (8H, m) 3.38 (2H, d, 7 Hz) 4.45 (2H, s) 6.7–8.23 (10H, m) 9.67 (1H, bs) 9.87 (1H, s) | Found Calcd. | 63.79% 63.75% | 6.63% 6.57% | 13.50% 13.52% |
| 23 | 148–50 | IR: 3470 3370 3270 1685 1645 NMR: 0.55–1.91 (11H, m) 3.13 (2H, d, 6 Hz) 4.30 (2H, s) 6.34–8.02 (10H, m) 9.33 (1H, s) 9.52 (1H, s) | Found Calcd. | 64.88% 64.77% | 6.55% 6.38% | 13.03% 13.14% |
| 24 | 194–5 | IR: 3460 3340 3250 1680 1630 1230 NMR*: 4.99 (2H, s) 6.82–7.87 (15H, m) 9.4 (1H, s) 9.67 (1H, s) | Found Calcd. | 65.04% 65.02% | 4.71% 4.71% | 13.71% 13.79% |
| 25 | 186–8 | IR: 3450 3410 3340 3240 1678 1630 NMR*: 4.97 (2H, s) 6.91–7.97 (14H, m) 9.4 (1H, s) 9.65 (1H, s) | Found Calcd. | 62.37% 62.26% | 4.09% 4.27% | 13.21% 13.20% |
| 26 | 202–4 | IR: 3430 3300 1690 1650 NMR: 5.05 (2H, s) 6.8–8.1 (14H, m) 9.55 (1H, bs) 9.79 (1H, s) | Found Calcd. | 60.06% 59.94% | 4.05% 4.12% | 12.91% 12.71% |
| 27 | 129–131 | IR: 3460 3340 3240 1680 1630 NMR: 4.46 (4H, s) 6.6–7 (1H, m) 7–8.08 (14H, m) 9.46 (1H, bs) 9.7 (1H, bs) | Found Calcd. | 65.62% 65.71% | 5.05% 5.03% | 13.52% 13.33% |

TABLE 2-continued

| Compound No. | Melting point (°C.) | IR (KBr,cm$^{-1}$) and NMR [d$_6$-DMSO, δ, ppm, 60 MHz] (*CDCl$_3$ was used) | | Elemental analysis | | |
|---|---|---|---|---|---|---|
| | | | Found Calcd. | C (%) | H (%) | N (%) |
| 28 | 163–4 | IR: 3475 3350 3250 1685 1635<br>NMR: 3.87 (2H, d, 5 Hz) 4.33 (2H, s)<br>4.87–5.37 (2H, m) 5.43–6.07 (1H, m)<br>6.40–7.93 (10H, m) 9.30 (1H, s)<br>9.50 (1H, s) | Found<br>Calcd. | 61.69%<br>61.62% | 5.37%<br>5.17% | 15.22%<br>15.13% |
| 29 | 169–70 | IR: 3460 3340 3240 1680 1630 1470<br>NMR*: 3.77 (2H, q, 9 Hz) 4.58 (2H, s)<br>5.4 (1H, bs) 6.7–7.57 (8H, m)<br>7.87–8.2 (1H, m) 9.87–10.27 (2H, m) | Found<br>Calcd. | 52.50%<br>52.43% | 4.11%<br>3.91% | 13.45%<br>13.59% |
| 30 | 133–5 | IR: 3460 3320 3230 1680 1630<br>NMR*: 3.76 (2H, tt, 13 Hz, 2 Hz) 4.56 (2H, s)<br>5.56 (1H, bs) 5.9 (1H, tt, 53 Hz, 6 Hz)<br>6.8–7.63 (8H, m) 7.8–8.3 (1H, m)<br>9.66–10.3 (2H, m) | Found<br>Calcd. | 51.16%<br>51.36% | 4.01%<br>3.86% | 12.69%<br>12.61% |
| 31 | 112–4 | IR: 3450 3320 3220 1680 1630<br>NMR*: 3.86 (2H, tq, 13 Hz, 2 Hz) 4.61 (2H, s)<br>5.53 (1H, bs) 6.73–7.73 (8H, m)<br>7.91–8.3 (1H, m) 9.63–10.3 (2H, m) | Found<br>Calcd. | 49.32%<br>49.36% | 3.41%<br>3.49% | 12.29%<br>12.12% |
| 32 | 103–5 | IR: 3460 3270 1680 1640<br>NMR: 4.13 (2H, tq, 14 Hz, 2 Hz) 4.65 (2H, s)<br>6.73–8.03 (10H, m) 9.83 (1H, s)<br>6.89 (1H, s) | Found<br>Calcd. | 49.26%<br>49.36% | 3.43%<br>3.49% | 12.33%<br>12.12% |
| 33 | 130–1 | IR: 3460 3260 1680 1630<br>NMR: 4.09 (2H, tq, 14 Hz, 2 Hz) 4.6 (2H, s)<br>6.57–7.73 (8H, m) 8.23 (2H, dd, 9 Hz, 6 Hz)<br>9.7 (1H, s) 9.82 (1H, s) | Found<br>Calcd. | 49.29%<br>49.36% | 3.42%<br>3.49% | 12.31%<br>12.12% |
| 34 | 125–7 | IR: 3460 3340 3220 1680 1630<br>NMR*: 3.53–4.08 (2H, m) 4.8 (2H, s)<br>4.93 (1H, d, 6-plet, 50 Hz, 6 Hz) 5.8 (1H, bs)<br>6.73–7.6 (8H, m) 7.91–8.31 (1H, m)<br>9.71–10.4 (2H) | Found<br>Calcd. | 48.76%<br>48.59% | 3.45%<br>3.47% | 11.38%<br>11.33% |
| 35 | 114–5 | IR: 3460 3350 3240 1680 1638<br>NMR: 4.13 (2H, tt, 14 Hz, 2 Hz) 4.64 (2H, s)<br>6.7–8.07 (10H, m) 9.3–9.93 (2H) | Found<br>Calcd. | 46.75%<br>46.89% | 3.16%<br>3.15% | 11.05%<br>10.93% |
| 36 | 110–2 | IR: 3460 3260 1680 1640 1580 1470<br>1220 NMR: 4.13 (2H, tt, 14 Hz, 2 Hz)<br>4.63 (2H, s) 6.7–8.07 (10H, m)<br>9.77 (1H, s) 9.83 (1H, s) | Found<br>Calcd. | 46.78%<br>46.89% | 3.15%<br>3.15% | 11.03%<br>10.93% |
| 37 | 124–6 | IR: 3470 3260 1680 1640 1600 1470<br>1230 NMR: 4.08 (2H, tt, 14 Hz, 2 Hz)<br>4.59 (2H, s) 6.63–7.63 (8H, m)<br>8.0 (2H, dd, 9 Hz, 6 Hz) 9.63 (1H, s)<br>9.73 (1H, s) | Found<br>Calcd. | 46.72%<br>46.89% | 3.17%<br>3.15% | 11.07%<br>10.93% |
| 38 | 101–3 | IR: 3460 3350 3240 1680 1635 1265<br>NMR: 4.13 (2H, tt, 14 Hz, 2 Hz) 4.65 (2H, s)<br>6.13 (1H, tt, 52 Hz, 6 Hz)<br>6.73–8.1 (10H, m) 9.47–9.9 (2H, m) | Found<br>Calcd. | 46.14%<br>46.33% | 3.16%<br>3.15% | 10.43%<br>10.29% |
| 39 | 108–10 | IR: 3475 3350 3240 1685 1635<br>NMR: 4.17 (2H, tt, 14 Hz, 2 Hz)<br>4.66 (2H, s) 6.32 (1H, tt, 55 Hz, 5 Hz)<br>6.6–8.23 (10H, m) 9.61 (1H, s)<br>9.87 (1H, s) | Found<br>Calcd. | 43.07%<br>42.87% | 2.86%<br>2.66% | 8.52%<br>8.69% |
| 40 | 124–5 | IR:3450 3260 1680 1635<br>NMR*: 0.86 (6H, d, 6 Hz) 1.1–1.83 (3H, m)<br>3.45 (2H, t, 6 Hz) 4.41 (2H, s) 5.5–5.83<br>(1H, bs) 6.65–7.3 (5H, m) 7.4 (2H, d, 9 Hz)<br>7.81 (2H, d, 9 Hz) 9.5 (1H, bs) 10.28 (1H, s) | Found<br>Calcd. | 60.30%<br>60.50% | 5.85%<br>6.04% | 13.26%<br>13.44% |
| 41 | 106–8 | IR: 3460 3310 1680 1640 1470 1200<br>NMR: 3.98 (2H, tq, 14 Hz, 2 Hz) 4.33 (2H, s)<br>6.63–7.57 (8H, m) 7.87 (2H, d, 8 Hz)<br>9.47–9.87 (2H, m) | Found<br>Calcd. | 47.51%<br>47.66% | 3.52%<br>3.37% | 11.56%<br>11.70% |
| 42 | 123–5 | IR: 3480 3270 1670 1640 1470 1220<br>NMR: 4.12 (2H, tt, 13 Hz, 2 Hz) 4.61 (2H, s)<br>6.83 (1H, bs) 6.97–7.27 (7H, m)<br>8.0 (2H, d, 8 Hz) 9.7 (1H, s) 9.77 (1H, s) | Found<br>Calcd. | 45.62%<br>45.43% | 2.89%<br>3.05% | 10.44%<br>10.59% |
| 43 | 97–100 | IR: 3460 3310 3250 1680 1630 1460 NMR*.<br>0.9 (6H, d, 6 Hz) 1.23–1.83 (3H, m) 2.41 (3H,<br>s) 3.46 (2H, t, 6 Hz) 4.45 (2H, s) 5.13–5.7<br>(1H, bs) 6.68–7.2 (5H, m) 7.26 (2H, d, 9 Hz)<br>7.81 (2H, d, 9 Hz) 9.5 (1H, bs) 10.4 (1H, bs) | Found<br>Calcd. | 66.49%<br>66.65% | 6.93%<br>7.12% | 14.14%<br>14.13% |
| 44 | 110–2 | IR: 3470 3320 3250 1680 1640 1470<br>1200 NMR: 2.37 (3H, s) 4.12 (2H, tq, 14 Hz,<br>2 Hz) 4.61 (2H, s) 6.67–7.63 (8H, m)<br>7.87 (2H, d, 8 Hz) 9.52 (1H, s) 9.73 (1H, s) | Found<br>Calcd. | 52.52%<br>52.41% | 4.02%<br>4.18% | 12.28%<br>12.22% |
| 45 | 110–2 | IR: 3470 3250 1680 1640 1470 1220<br>NMR: 2.3 (3H, s) 4.11 (2H, tt, 14 Hz, 2 Hz)<br>4.6 (2H, s) 6.67 (1H, bs) 6.97–7.67 (7H, m)<br>7.87 (2H, d, 8 Hz) 9.51 (1H, s) 9.7 (1H, s) | Found<br>Calcd. | 49.57%<br>49.61% | 3.76%<br>3.77% | 10.97%<br>11.02% |
| 46 | 100–2 | IR: 3460 3320 3240 1680 1630 | Found | 64.21% | 6.94% | 13.48% |

TABLE 2-continued

| Compound No. | Melting point (°C.) | IR (KBr,cm$^{-1}$) and NMR [d$_6$-DMSO, δ, ppm, 60 MHz] (*CDCl$_3$ was used) | Elemental analysis | | | |
|---|---|---|---|---|---|---|
| | | | | C (%) | H (%) | N (%) |
| | | NMR: 0.85 (6H, d, 6 Hz) 1.16–1.66 (3H, m) 3.41 (2H, t, 6 Hz) 3.81 (3H, s) 4.33 (2H, s) 6.6–7.65 (6H, m) 7.16 (2H, d, 9 Hz) 7.98 (2H, d, 9 Hz) 9.46 (1H, bs) 9.7 (1H, bs) | Calcd. | 64.06% | 6.84% | 13.58% |
| 47 | 128–30 | IR: 3460 3280 1680 1640 1600 1470 1320 NMR: 3.81 (3H, s) 4.12 (2H, tt, 15 Hz, 2 Hz) 4.6 (2H, s) 6.7–7.73 (8H, m) 8.0 (2H, d, 8 Hz) 9.55 (1H, s) 9.77 (1H, s) | Found Calcd. | 4823% 48.10% | 3.51% 3.65% | 10.69% 10.68% |

The compounds of the present invention represented by the formula (I) can be easily synthesized from a process according to the following Reaction Scheme 1, which comprises reacting phenylhydrazone derivative (II) of 2-oxazoline-4,5-dione with ammonia in an organic solvent such as acetone at a temperature of preferably −10° to 100° C. for 0.1 to 10 hours.

Reaction Scheme 1 (R$^1$ and R$^2$ are as defined above)

-continued
Reaction Scheme 1 (R$^1$ and R$^2$ are as defined above)

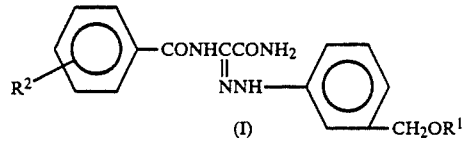

(I)

The phenylhydrazone derivatives (II) of 2-oxazoline-4,5-dione used as starting compound of the compounds of the present invention can be synthesized from a process according to the following Reaction Scheme 2:

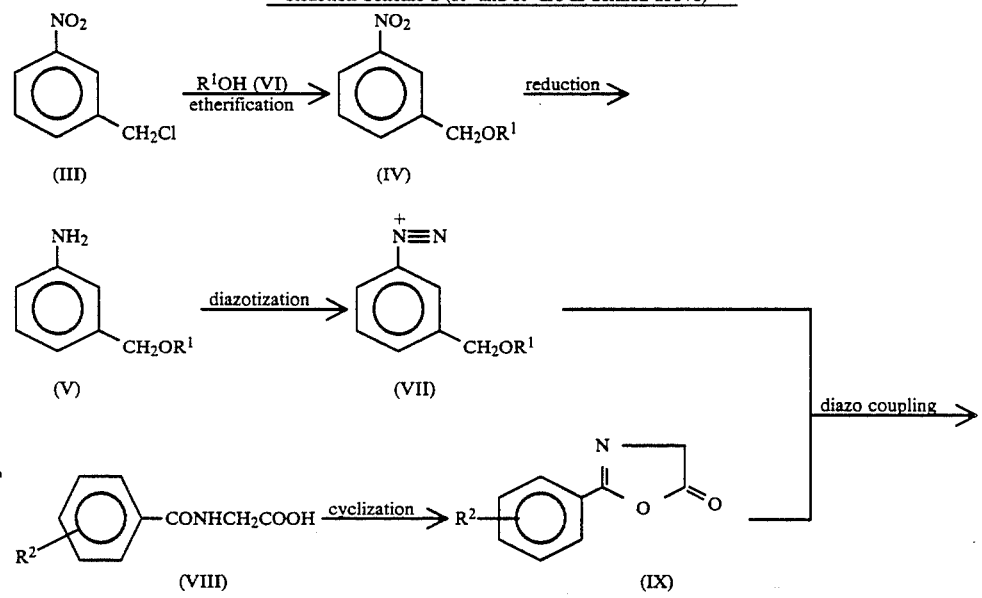

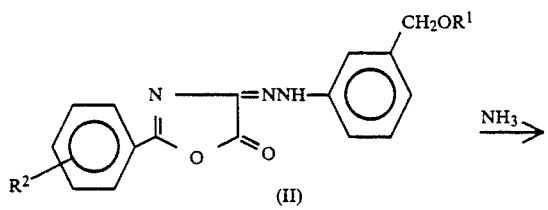

Nitrobenzyl chloride (III) is etherified by reacting with R$^1$OH (VI) in the presence of a hydrogen chloride acceptor such as KOH at a temperature of preferably −10° to 150° C. and then reduced by suitable method such as catalytic reduction to form an aniline derivative (V), and the aniline derivative (V) is then diazotized by a conventional method to synthesize a diazonium compound (VII).

Separately, a hippuric acid derivative (VIII) is subjected to dehydrating-cyclization by, for instance, reacting with acetic anhydride to synthesize a 2-oxazoline-5-one derivative (IX), and this derivative (IX) and the diazonium compound (VII) are subjected to diazo coupling at a temperature of preferably −50° to 100° C. to synthesize a phenylhydrazone derivative of 2-oxazoline-4,5-dione represented by the formula (II).

The phenylhydrazone derivative of oxamide according to the present invention can be used either singly or in combination with various types of carrier (diluent) and/or adjuvants commonly used in the preparation of agricultural chemicals, in the various forms of composition such as wettable powder, emulsion, granules, powder, etc.

The concentration of phenylhydrazone derivative of oxamide of the present invention in the compositions is preferably in the range of 0.1 to 50% by weight.

The phenylhydrazone derivatives of oxamide of the present invention and the herbicidal composition containing this compound as active ingredient can be sprayed on the field soil and/or to the stalks and leaves of plants by a conventional method so that the compound will be applied at a rate of preferably 0.1 to 500 g per 10 ares.

The present invention will hereinafter be described more precisely while referring to the following non-limitative examples.

SYNTHESIS EXAMPLE 1

Synthesis of 1-(3-methylbutoxy)methyl-3-nitrobenzene

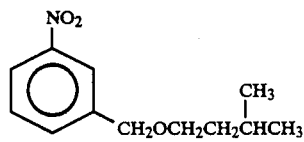

Seventy-eight g (1.39 mol, 1.5 equivalent) of KOH pellets were added into a solution prepared by dissolving 158.1 g (0.92 mol) of 3-nitrobenzyl chloride into a mixture of 500ml (4.59 mol, 5 equivalents) of 3-methyl-1-butanol and 140 ml of dimethylformamide under vigorous stirring while cooling the solution with a water bath. The temperature rose up to 43° C. but thereafter it lowered gradually to return to room temperature. The solution was stirred at room temperature for 7 hours to complete the reaction.

The solids in the reaction solution were filtered out. The filtrate was adjusted to pH 2 with hydrochloric acid and then excess alcohol and dimethylformamide were distilled off. The residue was dissolved in a mixed solvent of 450 ml of n-hexane and 50 ml of ethyl acetate, then washed with 1N HCl and a saturated sodium chloride solution successively and dried over magnesium sulfate. The solvent was distilled off and the residue was fractionally distilled. The fraction having a boiling point of 116°–117° C. (at 0.08 mmHg) was collected and 185.2 g of 1-(3-methylbutoxy)methyl-3-nitrobenzene was obtained in a 90.1% yield.

SYNTHESIS EXAMPLE 2

Synthesis of 3-[(3-methylbutoxy)methyl]aniline

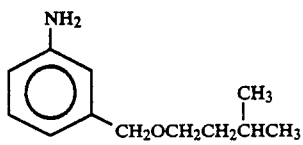

A hundred and thirty g (0.58 mol) of the nitrobenzene derivative obtained in Synthesis Example 1 was dissolved in 150 ml of ethanol, followed by the addition of 0.6 g of 10% palladium carbon. Under stirring, 89 ml (1.84 mol) of hydrazine hydrate was added dropwise to the solution at a rate which would not cause violent foaming. Thereafter, the mixed solution was refluxed on a hot water bath for 3 hours to complete the reaction. The filtrate was allowed to cool by itself and, after filtering out the catalyst, washed with ethanol. The filtrate was concentrated, dissolved in 300 ml of dichloromethane, washed with a 10% sodium carbonate solution and a saturated sodium chloride solution successively, and dried over anhydrous potassium carbonate. The solvent was distilled off and the residue was fractionally distilled. The fraction having a boiling point of 105°–106° C. (at 0.19 mmHg) was collected and 109.2 g of 3-[(3-methylbutoxy)methyl]aniline was obtained in a 97.1% yield.

SYNTHESIS EXAMPLE 3

Synthesis of 4-[3-[(3-methylbutoxy)methyl]phenyl]hydrazone of 2-(2-fluorophenyl)-2-oxazoline-4,5-dione

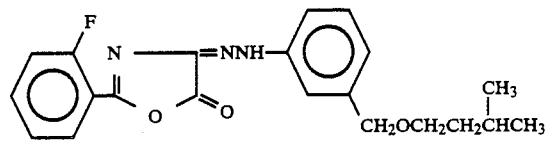

A solution of 3.94 g of 2-fluorohippuric acid and 3.28 g of sodium acetate in 17.4 ml of acetic anhydride was stirred at 60° C. for 20 minutes to prepare 2-(2-fluorophenyl)-2-oxazoline-5-one, and was quickly cooled with ice-water.

Separately, 3.48 g (18 mmol) of 3-[(3-methylbutoxy)methyl]aniline obtained in Synthesis Example 2 was dissolved in a mixture of 3.4 ml of 35% hydrochloric acid and 12 ml of acetic acid, and the solution was stirred under cooling with ice-water Then, the solution was added with 2.8 ml of isopentyl nitrite and further stirred for 10 minutes to prepare a diazonium salt.

The previously prepared mixture containing 2-(2-fluorophenyl)-2-oxazoline-5-one was stirred under cooling with ice-water, and the diazonium salt prepared above was added thereto over a period of 2 minutes, followed by stirring for 30 minutes. The solution was further stirred for 1.5 hour and then added with 40 ml of ice-water and 20 ml of petroleum ether, followed by 2-hour stirring. The orange-colored precipitate was filtered out and air-dried to obtain 2.45 g of the objective compound in a 35.5% yield.

EXAMPLE 1

Synthesis of 1-[3-[(3-methylbutoxy)methyl]phenyl]hydrazone of 1-(2-fluorobenzoyl)oxamide (Compound No. 17)

One and a half g of phenylhydrazone derivative of 2-oxazoline-4,5-dione synthesized in Synthesis Example 3 was added to 30 ml of ether and stirred at room temperature. The solution was added with 0.5 ml of a 35% $NH_3$ solution, stirred for 30 minutes and then added with 60 ml of hexane. The precipitate was filtered out and air dried to obtain 1.22 g of the objective compound having a melting point of 138°–140° C. in a 78% yield.

The phenyldyrazone derivatives of oxamide synthesized in the same way as described above from the various types of phenylhydrazone derivatives of 2-oxazoline-4,5-dione synthesized by the same process as Synthesis Examples 1–3 are shown in Table 1.

EXAMPLE 2

Preparation of wettable powder

Fifty parts of Compound No. 3, 5 parts of a salt of lignin sulfonic acid, 3 parts of a salt of alkylsulfonic acid and 42 parts of diatomaceous earth are mixed and pulverized to prepare a wettable powder. This wettable powder is diluted with water when used.

EXAMPLE 3

Preparation of emulsion

Twenty-five parts of Compound No. 10, 65 parts of xylene and 10 parts of polyoxyethylene alkylaryl ether are uniformly mixed to form an emulsion. This emulsion is diluted with water when used.

EXAMPLE 4

Preparation of granules

Eight parts of Compound No. 17, 40 parts of bentonite, 45 parts of clay and 7 parts of a salt of lignin sulfonic acid are uniformly mixed, further kneaded by adding water, granulated by an extrusion granulator and dried.

EXAMPLE 5

Effect on crop field weeds (pre-emergence treatment)

Soil was placed in a planters (650×210×220 mm) and flattened at the surface simulating a crop field. A prescribed amount of the seeds of *Amaranthus retroflexus, Bidens pilosa* var. *pilosa, Brassica arvensis, Stellaria media, Solanum nigrum, Abutilon theophrasti, Echinochloa Crus-galli* var. *frumentacea, Digitaria sanguinalis*, wheat and corn were sown and covered up with soil. Then the wettable powder prepared in the same way as Example 2 and diluted with water to a predetermined concentration was uniformly sprayed over the soil surface by a spray gun so that the active ingredient would be applied at a rate of 200 g/10 a. The planters were then left in a glasshouse to allow growth of the plants under control.

Twenty-one days after said treatment, the herbicidal effect of the compounds on the weeds and the phytotoxicity of the crops from the compounds were observed and evaluated according to the following ratings. The results are shown in Table 3.

| Ratings for evaluation |
|---|
| 0 . . . no effect |
| 1 . . . less than 30% herbicidal effect |
| 2 . . . 31–50% herbicidal effect |
| 3 . . . 51–70% herbicidal effect |
| 4 . . . 71–90% herbicidal effect |
| 5 . . . 91–100% herbicidal effect |
| Degree of damage |
| − : none, ± : slight, + : medium, |
| ++ : great, +++ : serious |

TABLE 3

| Compound No. | Amaranthus retroflexus | Bidens pilosa var. pilosa | Brassica arvensis | Stellaria media | Solanum nigrum | Abutilon theophrasti | Echinochloa Crus-galli var. frumentacea | Digitaria sanguinalis | Wheat | Corn |
|---|---|---|---|---|---|---|---|---|---|---|
| 1 | 5 | 5 | 5 | 5 | 5 | 5 | 5 | 5 | − | − |
| 2 | 5 | 5 | 5 | 5 | 5 | 5 | 5 | 5 | − | − |
| 3 | 5 | 5 | 5 | 5 | 5 | 5 | 5 | 5 | − | − |
| 4 | 5 | 5 | 5 | 5 | 5 | 5 | 5 | 5 | − | − |
| 5 | 4 | 4 | 5 | 5 | 5 | 5 | 4 | 5 | − | − |
| 6 | 5 | 4 | 5 | 5 | 5 | 4 | 4 | 4 | − | − |
| 7 | 5 | 4 | 5 | 5 | 4 | 5 | 4 | 5 | − | − |
| 8 | 5 | 5 | 5 | 5 | 5 | 5 | 4 | 4 | − | − |
| 9 | 5 | 5 | 5 | 5 | 5 | 5 | 5 | 5 | − | − |
| 10 | 5 | 5 | 5 | 5 | 5 | 5 | 5 | 5 | ± | ± |
| 11 | 5 | 5 | 5 | 5 | 5 | 5 | 5 | 5 | ± | + |
| 12 | 5 | 5 | 5 | 5 | 5 | 5 | 5 | 5 | ± | + |
| 13 | 5 | 5 | 5 | 5 | 5 | 5 | 5 | 5 | ± | + |
| 14 | 5 | 5 | 5 | 5 | 5 | 5 | 5 | 5 | − | ± |
| 15 | 5 | 5 | 5 | 5 | 5 | 5 | 5 | 5 | − | ± |
| 16 | 5 | 5 | 5 | 5 | 5 | 5 | 5 | 5 | − | ± |
| 17 | 5 | 5 | 5 | 5 | 5 | 5 | 4 | 5 | − | − |
| 18 | 5 | 5 | 5 | 5 | 5 | 5 | 5 | 5 | − | ± |
| 19 | 5 | 5 | 5 | 5 | 5 | 5 | 5 | 5 | − | ± |
| 20 | 5 | 5 | 5 | 5 | 5 | 5 | 4 | 5 | − | − |
| 21 | 5 | 5 | 5 | 5 | 5 | 5 | 5 | 5 | − | ± |
| 22 | 5 | 5 | 5 | 5 | 5 | 5 | 5 | 5 | − | ± |
| 23 | 5 | 5 | 5 | 5 | 5 | 5 | 5 | 5 | − | ± |
| 24 | 5 | 5 | 5 | 5 | 2 | 3 | 4 | 3 | − | − |
| 25 | 5 | 5 | 5 | 5 | 3 | 4 | 5 | 5 | − | − |
| 26 | 5 | 5 | 5 | 5 | 3 | 4 | 4 | 5 | − | − |
| 27 | 5 | 5 | 5 | 5 | 5 | 5 | 5 | 5 | − | ± |

TABLE 3-continued

| Compound No. | Amaranthus retroflexus | Bidens pilosa var. pilosa | Brassica arvensis | Stellaria media | Solanum nigrum | Abutilon theophrasti | Echinochloa Crusgalli var. frumentacea | Digitaria sanguinalis | Wheat | Corn |
|---|---|---|---|---|---|---|---|---|---|---|
| 28 | 5 | 5 | 5 | 5 | 5 | 5 | 5 | 5 | — | — |
| 29 | 5 | 5 | 5 | 5 | 5 | 5 | 5 | 5 | — | — |
| 30 | 5 | 5 | 5 | 5 | 5 | 5 | 5 | 5 | — | — |
| 31 | 5 | 5 | 5 | 5 | 5 | 5 | 5 | 5 | — | — |
| 32 | 5 | 5 | 5 | 5 | 5 | 5 | 5 | 5 | — | — |
| 33 | 5 | 5 | 5 | 5 | 5 | 5 | 5 | 5 | — | — |
| 34 | 5 | 5 | 5 | 5 | 5 | 5 | 5 | 5 | — | — |
| 35 | 5 | 5 | 5 | 5 | 5 | 5 | 5 | 5 | — | — |
| 36 | 5 | 5 | 5 | 5 | 5 | 5 | 5 | 5 | — | — |
| 37 | 5 | 5 | 5 | 5 | 5 | 5 | 5 | 5 | — | — |
| 38 | 5 | 5 | 5 | 5 | 5 | 5 | 5 | 5 | — | — |
| 39 | 5 | 5 | 5 | 5 | 5 | 5 | 5 | 5 | — | — |
| 40 | 5 | 5 | 5 | 5 | 4 | 4 | 5 | 5 | — | — |
| 41 | 5 | 5 | 5 | 5 | 4 | 4 | 5 | 5 | — | — |
| 42 | 5 | 5 | 5 | 5 | 5 | 5 | 5 | 5 | — | — |
| 43 | 4 | 5 | 5 | 5 | 3 | 5 | 4 | 5 | — | — |
| 44 | 5 | 5 | 5 | 5 | 4 | 4 | 4 | 5 | — | — |
| 45 | 4 | 5 | 5 | 5 | 4 | 5 | 4 | 5 | — | — |
| 46 | 3 | 4 | 4 | 4 | 2 | 3 | 2 | 2 | — | — |
| 47 | 3 | 4 | 4 | 5 | 3 | 4 | 3 | 3 | — | — |

EXAMPLE 6

Effect on crop field weeds (by post-emergence treatment)

The seeds of the specified plants were sown by following the same procedure as Example 5. When the plants have grown to the one- to two-foliage stage, the wettable powder prepared in the same way as Example 2 and diluted with water was uniformly sprayed to the stalks and leaves of the plants and on the soil surface by a spray gun so that the active ingredient would be applied at a rate of 200 g/10 a. Then the planters were left in a glasshouse to allow growth of the plants under control.

Twenty-one days after the treatment, the herbicidal effect of the compounds and phytotoxicity of the crops were observed and evaluated in the same way as in Example 5. The results are shown in Table 4.

TABLE 4

| Compound No. | Amaranthus retroflexus | Bidens pilosa var. pilosa | Brassica arvensis | Stellaria media | Solanum nigrum | Abutilon theophrasti | Echinochloa Crusgalli var. frumentacea | Digitaria sanguinalis | Wheat | Corn |
|---|---|---|---|---|---|---|---|---|---|---|
| 1 | 5 | 5 | 5 | 5 | 5 | 5 | 2 | 2 | — | — |
| 2 | 5 | 5 | 5 | 5 | 5 | 5 | 2 | 3 | — | ± |
| 3 | 5 | 5 | 5 | 5 | 4 | 4 | 2 | 2 | — | — |
| 4 | 5 | 5 | 5 | 5 | 4 | 3 | 2 | 2 | — | — |
| 5 | 5 | 5 | 5 | 4 | 4 | 3 | 1 | 2 | — | — |
| 6 | 3 | 4 | 5 | 4 | 2 | 4 | 1 | 2 | — | — |
| 7 | 5 | 5 | 5 | 5 | 3 | 5 | 2 | 2 | — | — |
| 8 | 5 | 5 | 5 | 5 | 5 | 5 | 2 | 2 | — | — |
| 9 | 3 | 5 | 4 | 4 | 3 | 4 | 1 | 2 | — | — |
| 10 | 5 | 5 | 5 | 5 | 5 | 5 | 3 | 2 | — | ± |
| 11 | 5 | 5 | 5 | 5 | 5 | 5 | 3 | 4 | — | ± |
| 12 | 5 | 5 | 5 | 5 | 5 | 5 | 3 | 3 | — | ± |
| 13 | 5 | 5 | 5 | 5 | 5 | 5 | 3 | 3 | — | ± |
| 14 | 3 | 5 | 5 | 5 | 3 | 4 | 2 | 2 | — | — |
| 15 | 5 | 5 | 5 | 5 | 4 | 5 | 2 | 2 | — | — |
| 16 | 5 | 5 | 5 | 5 | 4 | 5 | 2 | 2 | — | — |
| 17 | 4 | 5 | 4 | 3 | 5 | 5 | 2 | 2 | — | — |
| 18 | 4 | 5 | 5 | 5 | 5 | 5 | 2 | 2 | — | — |
| 19 | 5 | 5 | 5 | 5 | 4 | 5 | 2 | 2 | — | — |
| 20 | 4 | 5 | 4 | 3 | 5 | 5 | 2 | 2 | — | — |
| 21 | 5 | 5 | 5 | 5 | 4 | 4 | 2 | 2 | — | — |
| 22 | 5 | 5 | 5 | 4 | 3 | 3 | 2 | 2 | — | — |
| 23 | 4 | 5 | 5 | 4 | 4 | 3 | 2 | 2 | — | — |
| 24 | 3 | 2 | 5 | 3 | 2 | 5 | 1 | 2 | — | — |
| 25 | 5 | 5 | 5 | 5 | 3 | 5 | 2 | 2 | — | — |
| 26 | 5 | 5 | 5 | 5 | 4 | 5 | 3 | 3 | — | — |
| 27 | 5 | 5 | 5 | 5 | 5 | 5 | 3 | 3 | — | — |
| 28 | 5 | 5 | 5 | 5 | 5 | 5 | 3 | 3 | — | — |
| 29 | 5 | 5 | 5 | 5 | 4 | 5 | 2 | 2 | — | — |
| 30 | 5 | 3 | 5 | 5 | 5 | 5 | 2 | 2 | — | — |
| 31 | 5 | 5 | 5 | 5 | 5 | 5 | 3 | 3 | — | — |
| 32 | 5 | 5 | 5 | 5 | 5 | 5 | 4 | 3 | — | — |
| 33 | 5 | 5 | 5 | 5 | 4 | 5 | 3 | 3 | — | — |
| 34 | 5 | 3 | 5 | 5 | 5 | 5 | 2 | 2 | — | — |

TABLE 4-continued

| Compound No. | Amaranthus retroflexus | Bidens pilosa var. pilosa | Brassica arvensis | Stellaria media | Solanum nigrum | Abutilon theophrasti | Echinochloa Crus-galli var. frumentacea | Digitaria sanguinalis | Wheat | Corn |
|---|---|---|---|---|---|---|---|---|---|---|
| 35 | 5 | 5 | 5 | 5 | 5 | 5 | 3 | 3 | — | — |
| 36 | 5 | 5 | 5 | 5 | 5 | 5 | 4 | 4 | — | — |
| 37 | 5 | 5 | 5 | 5 | 5 | 5 | 3 | 4 | — | — |
| 38 | 5 | 5 | 5 | 5 | 5 | 5 | 3 | 3 | — | — |
| 39 | 5 | 5 | 5 | 5 | 4 | 5 | 3 | 2 | — | — |
| 40 | 5 | 5 | 5 | 5 | 3 | 4 | 2 | 2 | — | — |
| 41 | 5 | 5 | 5 | 5 | 4 | 4 | 2 | 3 | — | — |
| 42 | 5 | 5 | 5 | 5 | 5 | 4 | 3 | 4 | — | — |
| 43 | 3 | 5 | 5 | 5 | 2 | 5 | 2 | 2 | — | — |
| 44 | 4 | 5 | 5 | 5 | 3 | 5 | 2 | 2 | — | — |
| 45 | 4 | 5 | 5 | 5 | 2 | 5 | 2 | 2 | — | — |
| 46 | 2 | 2 | 2 | 2 | 1 | 3 | 1 | 2 | — | — |
| 47 | 2 | 2 | 2 | 2 | 2 | 3 | 2 | 2 | — | — |

EXAMPLE 7

Effect on paddy field weeds and phytotoxicity to rice plant

In the 1/2000-are Wagner pots packed with paddy field soil and watered to simulate a paddy field, the seeds of *Echinochloa Crus-galli* var. *hispidula*, *Scirpus juncoides* subsp. Hotarui, *Alisma canaliculatum*, *Monochoria vaginalis* and *Cyperus difformis* were sown and the tubers of *Sagittaria pygmaea* and *Cyperus serotinus* were planted. Further, two 2-foliage seedlings of rice plant (variety: Sasanishiki) were transplanted in the pots. Then the pots were left in a glass house to allow growth of the plants for three days. Then the emulsions prepared in the same way as Example 3 and diluted with water to a predetermined concentration were uniformly trickled down to the water surface in each pot so that the active ingredient would be applied at a rate of 200 g/10 a.

Twenty-one days after said treatment, the herbicidal effect of the compounds and the degree of phytotoxicity of the rice plants were examined and evaluated according to the same ratings as in Example 5.

TABLE 5

| Compound No. | Echinochloa Crus-galli var. hispidula | Scirpus juncoides subsp. Hotarui | Alisma canaliculatum | Monochoria vaginalis | Cyperus difformis | Sagittaria pygmaea | Cyperus serotinus | rice plant |
|---|---|---|---|---|---|---|---|---|
| 1 | 5 | 5 | 5 | 5 | 5 | 5 | 5 | — |
| 2 | 5 | 5 | 5 | 5 | 5 | 5 | 5 | — |
| 3 | 5 | 5 | 5 | 5 | 5 | 5 | 5 | — |
| 4 | 5 | 5 | 5 | 5 | 5 | 5 | 5 | — |
| 5 | 5 | 5 | 5 | 5 | 5 | 5 | 5 | — |
| 6 | 5 | 1 | 2 | 2 | 1 | 3 | 2 | — |
| 7 | 5 | 2 | 5 | 5 | 5 | 5 | 4 | — |
| 8 | 5 | 5 | 5 | 5 | 5 | 5 | 5 | — |
| 9 | 5 | 3 | 5 | 4 | 2 | 4 | 4 | — |
| 10 | 5 | 5 | 5 | 5 | 5 | 5 | 5 | — |
| 11 | 5 | 5 | 5 | 5 | 5 | 5 | 5 | — |
| 12 | 5 | 5 | 5 | 5 | 5 | 5 | 5 | — |
| 13 | 5 | 5 | 5 | 5 | 5 | 5 | 5 | — |
| 14 | 5 | 3 | 5 | 4 | 3 | 4 | 4 | — |
| 15 | 5 | 5 | 5 | 5 | 5 | 5 | 5 | — |
| 16 | 5 | 5 | 5 | 5 | 5 | 5 | 5 | — |
| 17 | 5 | 5 | 5 | 5 | 5 | 5 | 5 | — |
| 18 | 5 | 5 | 5 | 5 | 5 | 5 | 5 | — |
| 19 | 5 | 5 | 5 | 5 | 5 | 5 | 5 | — |
| 20 | 5 | 5 | 5 | 5 | 5 | 5 | 5 | — |
| 21 | 5 | 5 | 5 | 5 | 5 | 5 | 5 | — |
| 22 | 5 | 5 | 5 | 5 | 5 | 5 | 4 | — |
| 23 | 5 | 5 | 5 | 5 | 5 | 4 | 4 | — |
| 24 | 5 | 2 | 3 | 5 | 3 | 3 | 2 | — |
| 25 | 5 | 4 | 5 | 5 | 5 | 5 | 5 | — |
| 26 | 5 | 4 | 5 | 5 | 5 | 5 | 4 | — |
| 27 | 5 | 5 | 5 | 5 | 5 | 5 | 5 | — |
| 28 | 5 | 5 | 5 | 5 | 5 | 5 | 5 | — |
| 29 | 5 | 4 | 5 | 5 | 5 | 5 | 4 | — |
| 30 | 5 | 5 | 5 | 5 | 5 | 5 | 5 | — |
| 31 | 5 | 5 | 5 | 5 | 5 | 5 | 5 | — |
| 32 | 5 | 5 | 5 | 5 | 5 | 5 | 5 | — |
| 33 | 5 | 5 | 5 | 5 | 5 | 5 | 5 | — |
| 34 | 5 | 5 | 5 | 5 | 5 | 5 | 5 | — |
| 35 | 5 | 5 | 5 | 5 | 5 | 5 | 5 | — |
| 36 | 5 | 5 | 5 | 5 | 5 | 4 | 5 | — |
| 37 | 5 | 5 | 5 | 5 | 5 | 4 | 5 | — |
| 38 | 5 | 5 | 5 | 5 | 5 | 5 | 5 | — |
| 39 | 5 | 5 | 5 | 5 | 5 | 5 | 5 | — |
| 40 | 5 | 5 | 5 | 5 | 5 | 4 | 5 | — |

TABLE 5-continued

| Compound No. | Echinochloa Crus-galli var. hispidula | Scirpus juncoides subsp. Hotarui | Alisma canaliculatum | Monochoria vaginalis | Cyperus difformis | Sagittaria pygmaea | Cyperus serotinus | rice plant |
|---|---|---|---|---|---|---|---|---|
| 41 | 5 | 5 | 5 | 5 | 5 | 5 | 5 | — |
| 42 | 5 | 5 | 5 | 5 | 5 | 5 | 5 | — |
| 43 | 5 | 4 | 3 | 5 | 5 | 5 | 4 | — |
| 44 | 5 | 4 | 4 | 5 | 5 | 4 | 4 | — |
| 45 | 5 | 4 | 4 | 5 | 5 | 5 | 4 | — |
| 46 | 2 | 3 | 2 | 2 | 2 | 3 | 2 | — |
| 47 | 2 | 3 | 3 | 3 | 2 | 3 | 3 | — |

What is claimed is:

1. A phenylhydrazone derivative of oxamide represented by the formula (I):

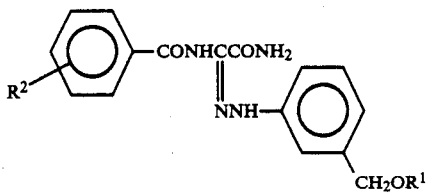

wherein $R^1$ is straight-chain alkyl group having 2 to 10 carbon atoms, branched alkyl group or cyclic alkyl group having 3 to 10 carbon atoms, alkyl group having 1 to 3 carbon atoms which is substituted with an alicyclic structure having 3 to 7 carbon atoms, phenyl group, halogen-substituted phenyl group, aralkyl group having 7 to 9 carbon atoms, alkenyl group having 3 to 6 carbon atoms, alkyl group having 2 to 4 carbon atoms which is substituted with alkoxy group having 1 to 4 carbon atoms, or alkyl group having 2 to 10 carbon atoms which is substituted with 1 to 19 fluorine atoms; and $R^2$ is hydrogen, fluorine, chlorine, methyl group or methoxy group.

2. The phenylhydrazone derivative according to claim 1, wherein $R^1$ is straight-chain alkyl group having 3 to 6 carbon atoms, branched alkyl group or cyclic alkyl group having 3 to 7 carbon atoms, alkyl group having 1 to 2 carbon atoms which is substituted with an alicyclic structure having 3 to 6 carbon atoms, phenyl group, halogen-substituted phenyl group, aralkyl group having 7 to 9 carbon atoms, alkenyl group having 3 to 6 carbon atoms, alkyl group having 2 carbon atoms which is substituted with alkoxy group having 4 carbon atoms, or alkyl group having 2 to 6 carbon atoms which is substituted with 3 to 12 fluorine atoms; and $R^2$ is hydrogen, fluorine, chlorine, methyl group or methoxy group.

3. The phenylhydrazone derivative according to claim 2, wherein $R^1$ is alkyl group having 2 to 4 carbon atoms which is substituted with 3 to 7 fluorine atoms and $R^2$ is hydrogen or fluorine.

4. The phenylhydrazone derivative according to claim 3, wherein said derivative is 1-[3-[(2,2,-trifluoroethoxy)methyl]phenyl]hydrazone of 1-benzoyloxamide.

5. The phenylhydrazone derivative according to claim 3, wherein said derivative is 1-[3-[(2,2,3,3-tetrafluoropropoxy)methyl]phenyl]hydrazone of 1-benzoyloxamide.

6. The phenylhydrazone derivative according to claim 3, wherein said derivative is 1-[3-[(2,2,2-trifluoroethoxy)methyl]phenyl]hydrazone of 1-(2-fluorobenzoyl)oxamide.

7. The phenylhydrazone derivative according to claim 3, wherein said derivative is 1-[3-[(2,2,3,3,3-pentafluoropropoxy)methyl]phenyl]hydrazone of 1-(2-fluorobenzoyl)oxamide.

8. The phenylhydrazone derivative according to claim 3, wherein said derivative is -[3-[(2,2,3,3,4,4,4-heptafluorobutoxy)methyl]pheny]hydrazone of 1-(2-fluorobenzoyl)oxamide.

9. A herbicidal composition comprising a herbicidally effective amount of a phenylhydrazone derivative of oxamide represented by the formula (I):

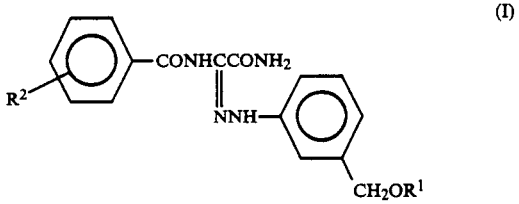

wherein $R^1$ is a straight-chain alkyl group having 2 to 10 carbon atoms, a branched alkyl group or cyclic alkyl group having 3 to 10 carbon atoms, an alkyl group having 1 to 3 carbon atoms which is substituted with an alicyclic structure having 3 to 7 carbon atoms, phenyl group, halogen-substituted phenyl group, aralkyl group having 7 to 9 carbon atoms, alkenyl group having 3 to 6 carbon atoms, alkyl group having 2 to 4 carbon atoms which is substituted with an alkoxy group having 1 to 4 carbon atoms, or an alkyl group having 2 to 10 carbon atoms which is substituted with 1 to 9 fluorine atoms; and $R^2$ is hydrogen, fluorine, chlorine, a methyl group or a methoxy group, and a herbicidally acceptable carrier or adjuvant.

* * * * *